(12) United States Patent
Wolter

(10) Patent No.: US 6,487,267 B1
(45) Date of Patent: Nov. 26, 2002

(54) X-RAY DIAGNOSTIC DEVICE FOR PRODUCING COMPUTED TOMOGRAPHY AND RADIOSCOPIC EXPOSURES

(75) Inventor: Ingbert Wolter, Gerhardshofen-Birnbaum (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 09/576,915

(22) Filed: May 23, 2000

(30) Foreign Application Priority Data

Jun. 18, 1999 (DE) .......................................... 199 27 953

(51) Int. Cl.[7] .............................................. G01N 23/00
(52) U.S. Cl. ............................................. 378/4; 378/19
(58) Field of Search ........................................ 378/4–20

(56) References Cited

U.S. PATENT DOCUMENTS

| | | | | |
|---|---|---|---|---|
| 4,174,481 A | * | 11/1979 | Liebetruth | 378/20 |
| 4,920,552 A | | 4/1990 | Hermens | |
| 4,965,726 A | * | 10/1990 | Heuscher et al. | 378/19 |
| 5,430,783 A | | 7/1995 | Hu et al. | |
| 6,041,097 A | * | 3/2000 | Roos et al. | 378/19 |

* cited by examiner

*Primary Examiner*—Craig E. Church
(74) *Attorney, Agent, or Firm*—Schiff Hardin & Waite

(57) ABSTRACT

An x-ray diagnostic apparatus allows computed tomography exposures to be prepared in a first operating mode, and radioscopic exposures in a second operating mode.

5 Claims, 2 Drawing Sheets

X-RAY DIAGNOSTIC DEVICE FOR PRODUCING COMPUTED TOMOGRAPHY AND RADIOSCOPIC EXPOSURES

BACKGROUND OF THE INVENTION

1. Field of the Invention

The present invention is directed to an x-ray diagnostic device of the type having a radiation emitter with a beam gating arrangement allocated thereto, a multi-line radiation detector for the production of electrical signals dependent upon the intensity of incident radiation, wherein the radiation emitter and the multi-line radiation detector are arranged opposite one another and can be rotated around a common center in a first operating mode and are stationary in a second operating mode.

2. Description of the Prior Art

An x-ray diagnostic device of the above type, implemented as a computed tomography apparatus, is known from U.S. Pat. No. 5,430,783.

Radiation examinations can be performed on an examination subject with such an x-ray diagnostic device and cross-sectional or overview exposures of the examined region of the examination subject can be shown on a display device from the signals of the radiation detector after processing with a signal processing chain.

A dynamic representation of anatomical subjects in the full field and in real time is not possible due to the relatively narrowly gated useful x-ray beam. A dynamic representation in the full field can only ensue off-line after a successful reconstruction of the signals (acquired in the computed tomography scanning) by an image computer in the signal processing chain. It is, however, desirable to make a combination of the dynamic realtime-imaging (radioscopy) with the advantages of the computed tomography (high contrast resolution by means of narrow gating of the useful x-ray beam) available to radiologists and physicians, particularly for interventional procedures in the human body using catheters and surgical instruments.

A dynamic representation of anatomical subjects in the full field and in real time is not attainable even with an x-ray examination apparatus as disclosed in U.S. Pat. No. 4,920, 562 which, besides an operating mode corresponding to that described in the aforementioned U.S. Pat. No. 5,430,783, also has a second operating mode, wherein the x-ray examination apparatus operates as a slotted imaging device. Even so, only a narrow slot is gated, corresponding to the slot width employed in computed tomography, but with the exception that the imaging devices do not rotate around the patient. Radioscopic exposures for overview images of the complete subject cannot be attained with the slotted imaging device.

SUMMARY OF THE INVENTION

An object of the present invention is to provide an x-ray diagnostic device of the type initially described, but which allows both dynamic real time imaging (radioscopy) and computed tomography exposures having a high contrast resolution to be made available to the user, with these functions being united in a single x-ray diagnostic device.

The above object is achieved in accordance with the principles of the present invention in an x-ray diagnostic device having a radiation emitter with a controllable gating arrangement allocated thereto, which gates an x-ray beam emitted by the radiation emitter, a multi-line radiation detector for producing electrical signals dependent on the intensity of radiation incident thereon, the radiation emitter and the detector being disposed opposite each other and being rotatable together around a common center in a first operating mode, the gating arrangement in the first operating mode being operated to produce a narrow fan beam and, in a second operating mode of the diagnostic device, the controllable gating arrangement being operated to produce an x-ray beam which substantially completely irradiates the multi-line radiation receiver.

By being able to produce both computed tomography exposures and real time radiographic images with the same device, space savings are achieved, as well as cost savings.

DESCRIPTION OF THE PREFERRED EMBODIMENTS

Figure 1:
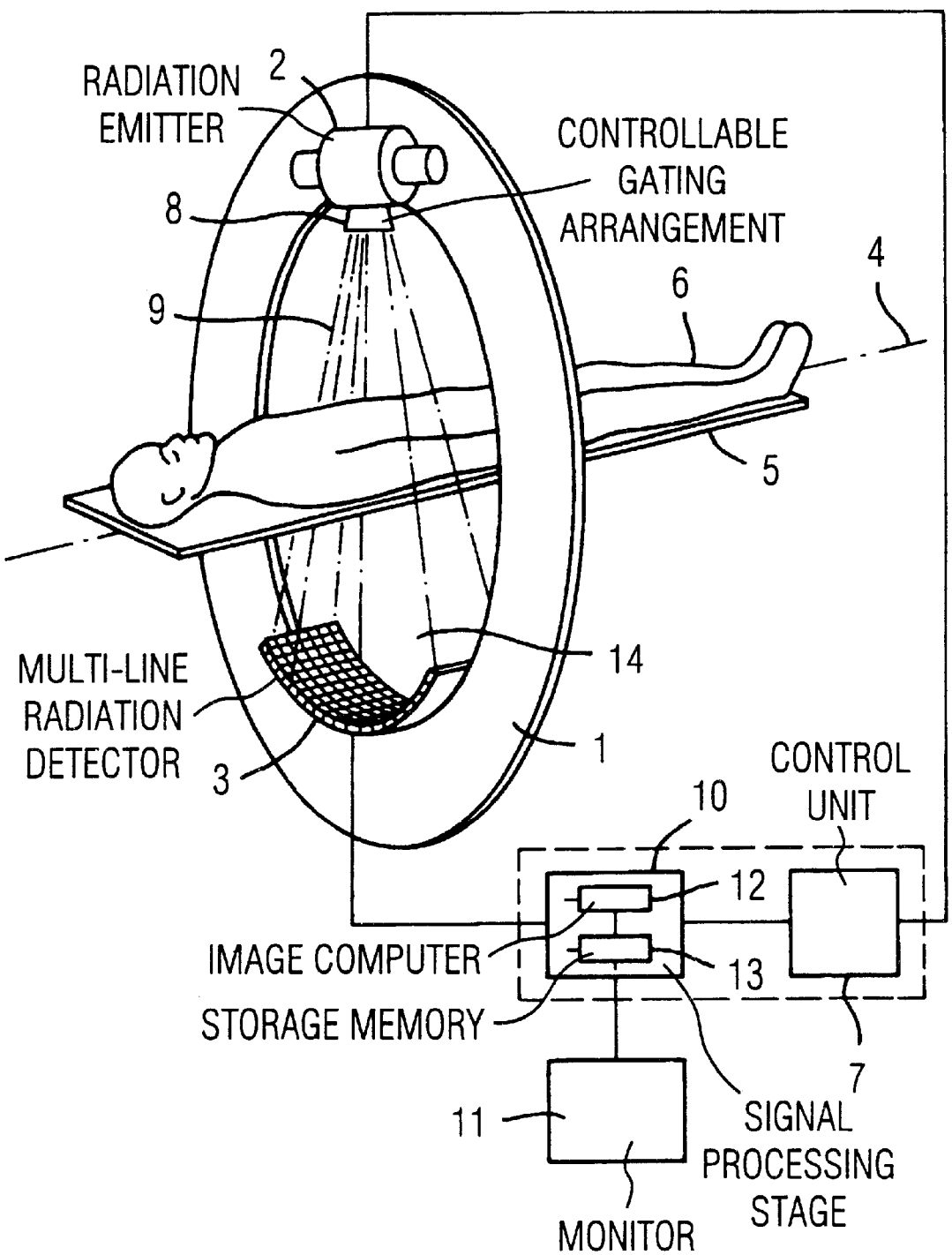
FIG. 1 is a schematic illustration of an x-ray diagnostic device according to the invention.

The x-ray diagnostic device in FIG. 1 has an exposure unit formed by a gantry at which a radiation emitter 2 and a multi-line radiation detector 3 are arranged opposite one another. The gantry 1 can be rotated around a central axis 4, for which purpose bearings, not shown in detail, and controllable drive means are provided in a known manner. Also shown is a positioning plate 5, upon which an examination subject 6 can be arranged. For an x-ray examination of the examination subject 6 using the radiation emitter 2 and the multi-line radiation detector 3, these are rotated around the central axis 4 and the radiation emitter 2 is energized via a control unit 7 for the emission of radiation. The radiation emitted from the radiation emitter 2 is gated into a narrow fan beam 9 via a controllable gating arrangement 8 allocated to the radiation emitter 2. The fan beam 9 penetrates the examination subject 6 and the attenuated radiation is incident on the multi-line radiation detector 3. The x-ray shadow image of the examination subject 6 is converted by the multi-line radiation detector 3 into electrical signals that are forwarded to a signal processing stage 10. On the basis of the signals of the multi-line radiation detector 3, image signals are produced by the signal processing stage 10 so that the image of the subject 6 is displayed at a monitor 11. The signal processing stage 10 includes, for this purpose, an image computer 12 and a storage memory 13 so that computed tomography images as well as overview exposures can be prepared on the basis of the signals acquired in the radiation scanning. For the preparation of overview exposures, however, it is required in a known for a relative movement to ensue between the exposure unit and the examination subject, without rotating the exposure unit. This manner of examination (imaging) defines a first operating mode of the x-ray diagnostic device.

In a second, selectable operating mode of the x-ray diagnostic device, the radiation emitter 2 and the multi-line radiation detector 3 are stationary and the radiation emitted from the radiation emitter 2 is gated by the controllable gating arrangement 8 to form an x-ray means 14 which covers the full width of the multi-line detector 3 along the direction of the axis 4, and the full angle of the detectors. In this operating mode, radioscopic exposures of the examination subject 6 are also prepared from various projection directions. The dynamic representation of anatomical subjects in the full field thus is possible in real time. The inventive x-ray diagnostic device unites dynamic real time imaging (radioscopy) with the advantages of computed tomography (high contrast resolution by narrow gating of the useful x-ray beam) for interventional procedures in the human body using catheters and surgical instruments.

Figure 2:
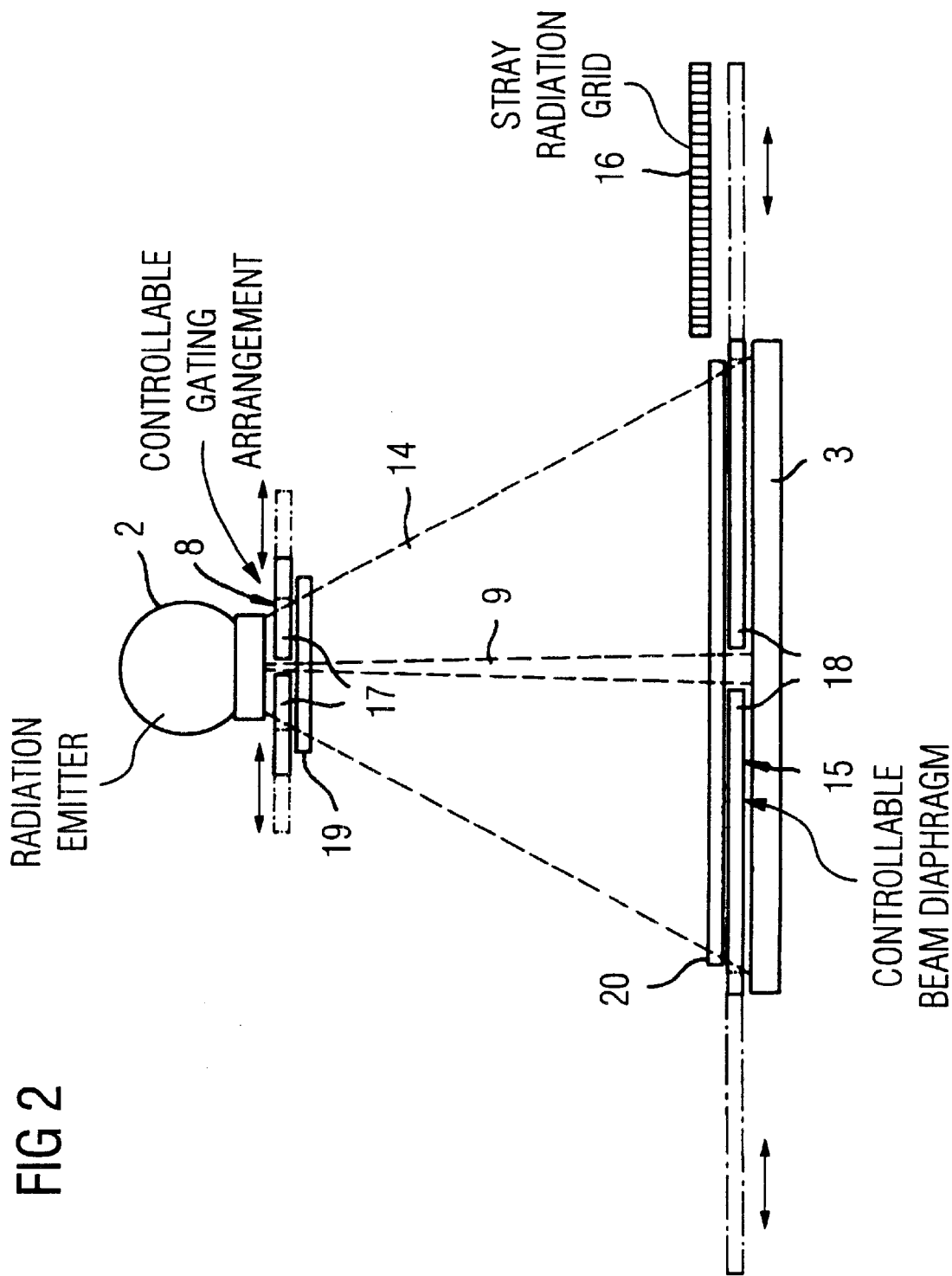
FIG. 2 shows details of the x-ray diagnostic device according to FIG. 1.

As can be seen from FIG. 2, another controllable beam diaphragm 15 is allocated to the multi-line radiation detector 3, the diaphragm plate of which passes only a slim band of the multi-line radiation detector 3 for the beam fan 9 in the first operating mode so that deterioration of the image caused by stray radiation is particularly avoided. In the second operating mode, the diaphragm plates of the controllable gating arrangement 8 and those of the controllable beam diaphragm 15 are adjusted, for example, in the position shown in the dotted line so that the x-ray beam 14 proceeds from the radiation transmitter 2 for radioscopy. To avoid disturbing signals that are produced due to stray radiation, a stray radiation grid 16 is preferably provided that can be moved to a position in front of the multi-line radiation detector 3 in the second operating mode. The controllable gating arrangement 8 and the controllable beam diaphragm 15 can include not only the indicated diaphragm plate pairs 17 and 18, respectively, but also can include diaphragm plate pairs 19 and 20, respectively, by which a gating of the radiation emitted from the radiation emitter 2 is possible on a quadratic or rectangular-shaped projection surface.

In the scope of the invention, the multi-line radiation detector 3 is preferably a solid-state detector, dimensioned such that a coverage of human anatomy is possible up to 45×45 cm, for example. The multi-line radiation detector 3 is preferably arced such that the distance between the surface of the multi-line radiation detector 3 and the focus of the radiation emitter 2 is substantially constant. It is, however, also possible to provide a planar radiation receiver, but then correction calculations are required due to the non-constant distance between the surface and the focus. Moreover, if the gantry 1 can be tilted with respect to the central axis 4, then diagonal projections also can be implemented.

Although modifications and changes may be suggested by those skilled in the art, it is the intention of the inventor to embody within the patent warranted hereon all changes and modifications as reasonably and properly come within the scope of his contribution to the art.

I claim as my invention:

1. An x-ray diagnostic apparatus comprising:

a radiation emitter which emits x-rays;

a controllable gating arrangement disposed in a path of said x-rays for gating said x-rays;

a patient table adapted to receive a patient thereon disposed in said path of said x-rays;

a multi-line solid-state radiation detector disposed for detecting x-ray which have proceeded through said patient, for producing electrical signals dependent on an intensity of said x-rays incident thereon;

a rotatable gantry on which said radiation emitter and said multi-line solid-state radiation detector are mounted opposite each other;

a signal processor connected to said multi-line solid-state radiation detector for processing said electrical signals;

a display monitor connected to said signal processor; and a control unit connected to said gantry, said radiation emitter and said signal processor for, in a first operating mode, rotating said gantry around a common center between said radiation emitter and said multi-line solid-state radiation detector, and operating said gating arrangement to produce a narrow fan beam of said x-rays, so that said electrical signals represent a plurality of projection data sets, and for operating said signal processor to generate a CT image from said projection data sets for display on said display monitor, and in a second operating mode, for maintaining said gantry and said patient table stationary and for operating said gating arrangement to produce an x-ray beam of said x-rays which is incident on substantially an entirety of said multi-line solid-state radiation detector, and for operating said signal processor to convert said electrical signals into a real time, two-dimensional image for display on said display monitor.

2. An x-ray diagnostic device as claimed in claim 1 further comprising means for selectively switching between said first operating mode and said second operating mode.

3. An x-ray diagnostic device as claimed in claim 2 wherein said control unit controls a size of said x-ray beam in said second operating mode is by operating said gating arrangement.

4. An x-ray diagnostic apparatus as claimed in claim 1 further comprising a controllable beam diaphragm disposed in front of said multi-line radiation detector, and wherein said control unit controls said controllable beam diaphragm dependent on said first operating mode and said second operating mode.

5. An x-ray diagnostic apparatus as claimed in claim 1 further comprising a stray radiation grid movable by said control unit to a position in front of said multi-line radiation detector in said second operating mode.

* * * * *